(12) United States Patent
Keller et al.

(10) Patent No.: US 6,852,130 B2
(45) Date of Patent: Feb. 8, 2005

(54) ANKLE-JOINT ENDOPROSTHESIS

(75) Inventors: Arnold Keller, Kayhude (DE); Hakon Kofoed, Charlottenlund (DK)

(73) Assignee: Waldemar Link GmbH & Co. KG, Hamburg (DE)

(*) Notice: Subject to any disclaimer, the term of this patent is extended or adjusted under 35 U.S.C. 154(b) by 0 days.

(21) Appl. No.: 10/382,989

(22) Filed: Mar. 7, 2003

(65) Prior Publication Data

US 2003/0181985 A1 Sep. 25, 2003

(30) Foreign Application Priority Data

Mar. 8, 2002 (EP) .................................. PCT/EP 02/02573

(51) Int. Cl.$^7$ .................................................. A61F 2/42
(52) U.S. Cl. .................................................. 623/21.18
(58) Field of Search ...................... 623/11.11, 16.11, 623/18.11, 21.11, 21.18, 23.39, 23.42

(56) References Cited

U.S. PATENT DOCUMENTS 4,755,185 A  7/1988  Tarr 5,824,106 A * 10/1998  Fournol .................... 623/21.18

FOREIGN PATENT DOCUMENTS

| DE | 88 12 806 U | 5/1989 |
| EP | 1 097 680 A1 | 9/2001 |
| FR | 2 676 917 | 12/1992 |
| FR | 2 684 291 | 6/1993 |
| WO | WO 00/69373 | 11/2000 |
| WO | WO 01/89427 A1 | 11/2001 |

* cited by examiner

Primary Examiner—Todd E. Manahan
Assistant Examiner—Anuradna Ramana
(74) Attorney, Agent, or Firm—Morrison & Foerster LLP

(57) ABSTRACT

An endoprosthesis for replacement of the ankle joint includes a component which is to be connected to the anklebone and which forms an upper slide surface a component which is to be connected to the tibia and which forms a lower slide surface, and a middle part. The middle part forms two slide surfaces which interact with slide surfaces on the tibial component and the anklebone component. In frontal section, the middle part is wedge-shaped with a wedge angle of between 1° and 12°.

5 Claims, 1 Drawing Sheet

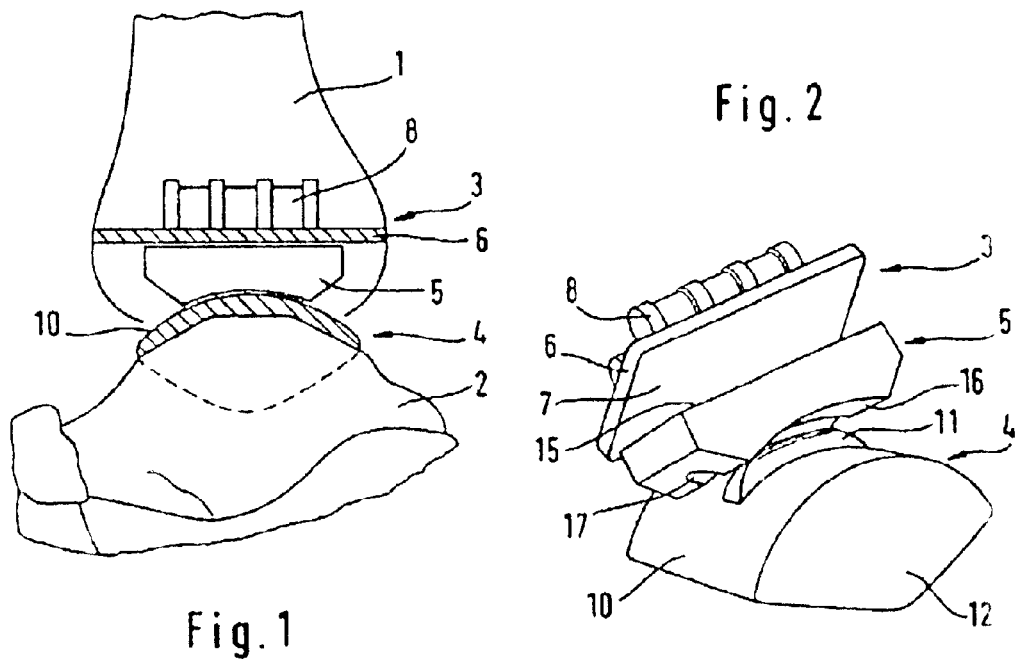
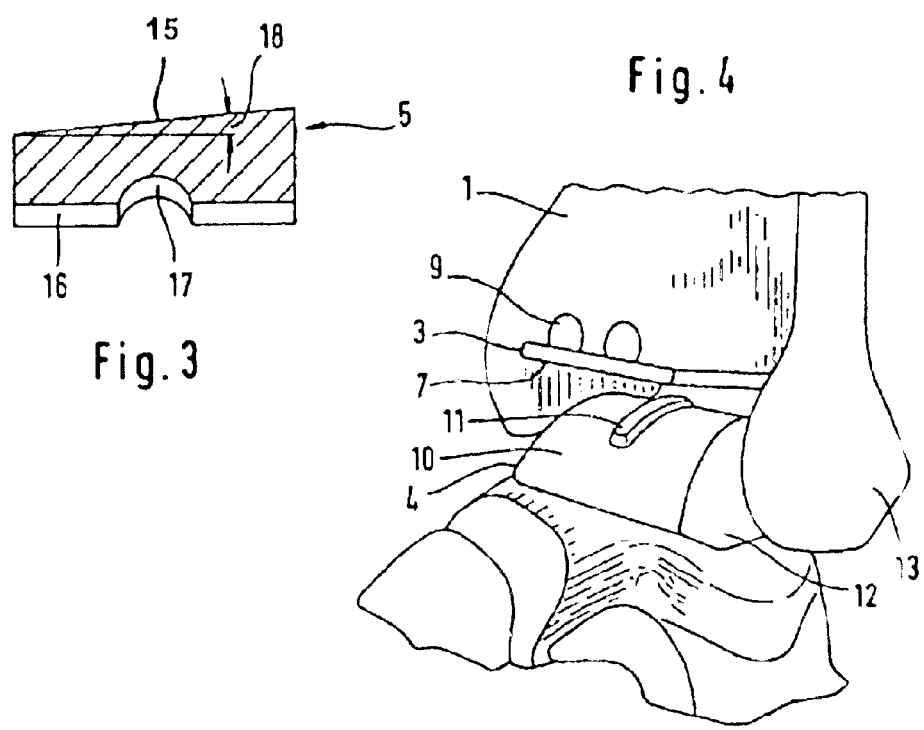

ANKLE-JOINT ENDOPROSTHESIS

FIELD AND BACKGROUND OF THE INVENTION

For replacement of the ankle joint, an endoprosthesis is known which consists of a component to be connected to the anklebone, a component to be connected to the tibia, and a middle part (DE-U-8812806; brochure entitled "LINK S.T.A.R. Totale Sprunggelenkprothese [H. Kofoed] by the company Waldemar Link (flexion and extension in the sagittal plane. The tibial component and the middle part form interacting slide surfaces which permit a rotation about the vertical axis. They can be made flat in order to GmbH & Co.), Hamburg). The anklebone component and the middle part interact via slide surfaces which permit compensating movements in the AP (anterior-posterior) direction and LM (lateral-medial) direction. Stabilization is effected by means of the natural ligament apparatus.

In the known prosthesis, the upper and lower slide surfaces of the middle part are oriented parallel to one another in the frontal plane. This is logical insofar as the aim is to replace the natural slide surfaces of the anklebone and of the tibia with the prosthetic slide surfaces, without any associated change in direction. However, it has been found that, after surgery, the collateral and medial ligaments of the ankle often have different tensioning, which can cause difficulties.

SUMMARY OF THE INVENTION

The invention makes it possible to avoid this imbalance by means of the fact that a middle part is provided which is wedge-shaped in the frontal plane. The directional axes of the slide surfaces in the frontal plane do not extend parallel to one another but at an angle which is normally between 1° and 12°. Depending on the anatomical conditions found, the physician can determine what angle, if any, he wishes to provide between the joint axes and does this by selecting the appropriate middle part. This can also be done during surgery.

To ensure that the middle part remains correctly oriented in respect of its wedge shape, its orientation is expediently fixed by way of the anklebone or the tibia, by means of the interacting slide surface pairs being designed in a manner which defines its direction. The joint between the anklebone and the middle part is particularly suitable for this.

In one embodiment of the invention, a system of endoprostheses for replacement of the ankle joint is used. The system includes various endoprostheses, each of which has an anklebone component configured to be connected to an anklebone and having an upper slide surface. Each endoprostheses also has a tibial component, configured to be connected to a tibia, having a lower slide surface. Each endoprosthesis also has a middle part. Each middlepart has two slide surfaces which are configured to interact with the slide surfaces of the anklebone and tibial components. Additionally, two or more middle parts of the endoprostheses are different from one another and have different wedge angles between their respective two slide surfaces.

The invention is explained in more detail below with reference to the drawing which depicts an advantageous illustrative embodiment. In the drawing:

BRIEF DESCRIPTION OF THE DRAWINGS

FIG. 1 shows a sagittal section through the joint fitted with the prosthesis,

FIG. 2 shows the prosthesis in a perspective view and opened out,

FIG. 3 shows a frontal section through the middle part, and

FIG. 4 shows a perspective view of the arrangement of bones and associated prosthesis parts before insertion of the middle part.

DETAILED DESCRIPTION OF THE INVENTION

The prosthesis consisting of the tibial component 3, the anklebone component 4 and the middle part 5 is to be arranged between the tibia 1 and the anklebone 2. The tibial component 3 has a plate-like part 6 whose underside 7 forms a flat slide surface. Projections 8 serve to secure it in corresponding resected cavities 9 in the tibia 1.

The anklebone component 4 forms a convexly curved slide surface 10 which can be of cylindrical or conical design. It has a rib 11 which lies in the direction of the relative movement of the middle part upon the flexion and extension movement. The anklebone component also has lateral facets 12 for interacting with corresponding slide surfaces of the tibia 1 and of the fibula 13.

The middle part 5 has a flat top 15 matching the slide surface 7, and a lower slide surface 16 which is designed congruent with the slide surface 10 of the anklebone component 4. It has a groove 17 for receiving the rib 11. In this way, the middle part 5 is guided laterally in relation to the anklebone component 4. Only flexion and extension movements are permitted.

The components 3 and 4 are expediently made of metal, and the middle part 5 of a plastic with good slide properties, such as polyethylene. However, other materials with sufficient strength and sliding capacity can be used, for example ceramics.

As a result of the congruent shape of the slide surfaces 10 and 16 and the rib 11 interacting with the groove 17, the middle part 5 is not rotatable relative to the ankle-joint component 4 about the vertical axis. Its orientation is therefore fixed by that of the anklebone component. While the embodiment shown completely excludes such rotation movements, embodiments are also conceivable in which this is only inhibited by the design of the slide surfaces, for example by these being of ellipsoid shape.

In the frontal section according to FIG. 3, the middle part is of wedge-shaped design. Its upper slide surface 15 encloses, with the direction of the lower slide surface 16, a wedge angle 18 which is preferably between 1° and 12°. In most cases it is between 3° and 8°.

As soon as the operating surgeon has implanted the tibial component 3 and the anklebone component 4, as is shown in FIG. 4, he can use suitable instruments to determine whether their slide surfaces 7 and 10 extend parallel or at an angle to one another in the LM direction when the collateral ligaments are tensioned. He chooses a suitable middle part 5 on this basis.

What is claimed is:

1. An endoprosthesis for replacement of the ankle joint, comprising an anklebone component configured to be connected to an anklebone and having an upper slide surface formed thereon, a tibial component configured to be connected to a tibia having a lower slide surface formed thereon and a middle part having two slide surfaces formed thereon and configured to interact with the slide surfaces of the anklebone and tibial components, wherein the middle part has a first lateral side and a second lateral side and is formed such that the first lateral side has a height greater than a height of the second lateral side in a frontal plane so that the two slide surfaces on the middle part are not parallel.

2. The endoprosthesis for replacement of the ankle joint as claimed in claim 1, wherein the upper slide surface on the anklebone component and a corresponding slide surface on the middle part interact substantially nonrotatably with respect to a vertical axis of the endoprosthesis.

3. The endoprosthesis as claimed in claim 1, wherein the lower slide surface on the tibial component and a corresponding slide surface on the middle part interact rotatably with respect to a vertical axis of the endoprosthesis.

4. The endoprosthesis as claimed in claim 1, 2 or 3, wherein the middle part has a wedge angle between the two slide surfaces of between 1° and 12°.

5. A system of endoprostheses for replacement of the ankle joint comprising a plurality of endoprostheses, each of said endoprostheses comprising an anklebone component configured to be connected to an anklebone and having an upper slide surface formed thereon, a tibial component configured to be connected to a tibia having a lower slide surface formed thereon and a middle part having two slide surfaces formed thereon and configured to interact with the slide surfaces of the anklebone and tibial components, wherein two or more middle parts of the endoprostheses are different from one another and have different wedge angles between their respective two side surfaces.

* * * * *